United States Patent
Brinon

[19]

[11] Patent Number: 5,879,336
[45] Date of Patent: Mar. 9, 1999

[54] DEVICE FOR INJECTING A LIQUID

[75] Inventor: Thierry Brinon, Montsoult, France

[73] Assignee: Vygon, Ecouen, France

[21] Appl. No.: 614,227

[22] Filed: Mar. 12, 1996

[30] Foreign Application Priority Data

Mar. 13, 1995 [FR] France .................................. 95 02874

[51] Int. Cl.⁶ .................................................. A61M 5/00
[52] U.S. Cl. .......................... 604/191; 604/184; 604/208; 604/213; 604/215; 604/231; 604/232; 604/236
[58] Field of Search ..................................... 604/181, 182, 604/183, 190, 191, 19, 48, 68, 203, 220, 70–73, 226, 236, 184, 186, 187, 237, 218, 231, 110, 111, 207, 208, 213, 215, 209, 210, 118, 121, 211, 232, 234–238, 245–249, 260; 222/325, 326, 327, 391

[56] References Cited

U.S. PATENT DOCUMENTS

| | | | |
|---|---|---|---|
| 1,272,742 | 7/1918 | Weguelin et al. | 604/226 |
| 2,475,939 | 7/1949 | Applezweig | 604/211 |
| 3,749,084 | 7/1973 | Cucchiara | 604/191 |
| 3,892,237 | 7/1975 | Steiner | 604/190 |
| 4,755,169 | 7/1988 | Sarnoff et al. | 604/191 |
| 5,032,117 | 7/1991 | Motta | 604/191 |
| 5,067,948 | 11/1991 | Haber et al. | 604/232 |
| 5,181,909 | 1/1993 | McFarlane | 604/226 |
| 5,300,041 | 4/1994 | Haber et al. | 604/207 |
| 5,372,586 | 12/1994 | Haber et al. | 604/191 |
| 5,499,751 | 3/1996 | Meyer | 604/190 |

FOREIGN PATENT DOCUMENTS

| | | |
|---|---|---|
| 483 759 | 10/1991 | European Pat. Off. . |
| 483759 | 5/1992 | European Pat. Off. . |
| 9107574 | 9/1991 | Germany . |
| 93-24160 | 12/1993 | WIPO . |
| 9324160 | 12/1993 | WIPO . |

*Primary Examiner*—Ronald Stright
*Attorney, Agent, or Firm*—McDermott, Will & Emery

[57] ABSTRACT

The invention relates to a portable and non-implantable device to enable a patient to self-administer, on demand, successive doses of a liquid while ensuring that the period of time between two successive administrations cannot be less than a reference value. The device has a liquid reservoir formed in a piston which can be pushed in a chamber to expel the contents of the chamber via an injection outlet and which is returned in the opposite direction by a return. The liquid reservoir communicates with the inside of the chamber via a passage formed through the piston and is provided with a flow rate limiter so that the time required to fill the chamber corresponds to a reference value. The invention is suitable for medical applications.

23 Claims, 3 Drawing Sheets

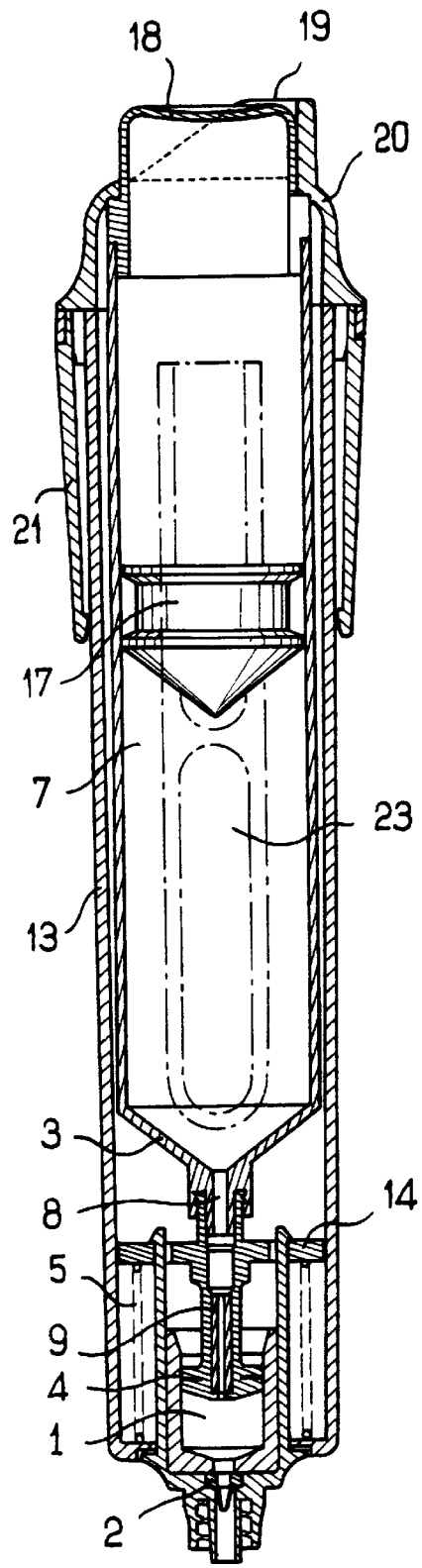
FIG_1
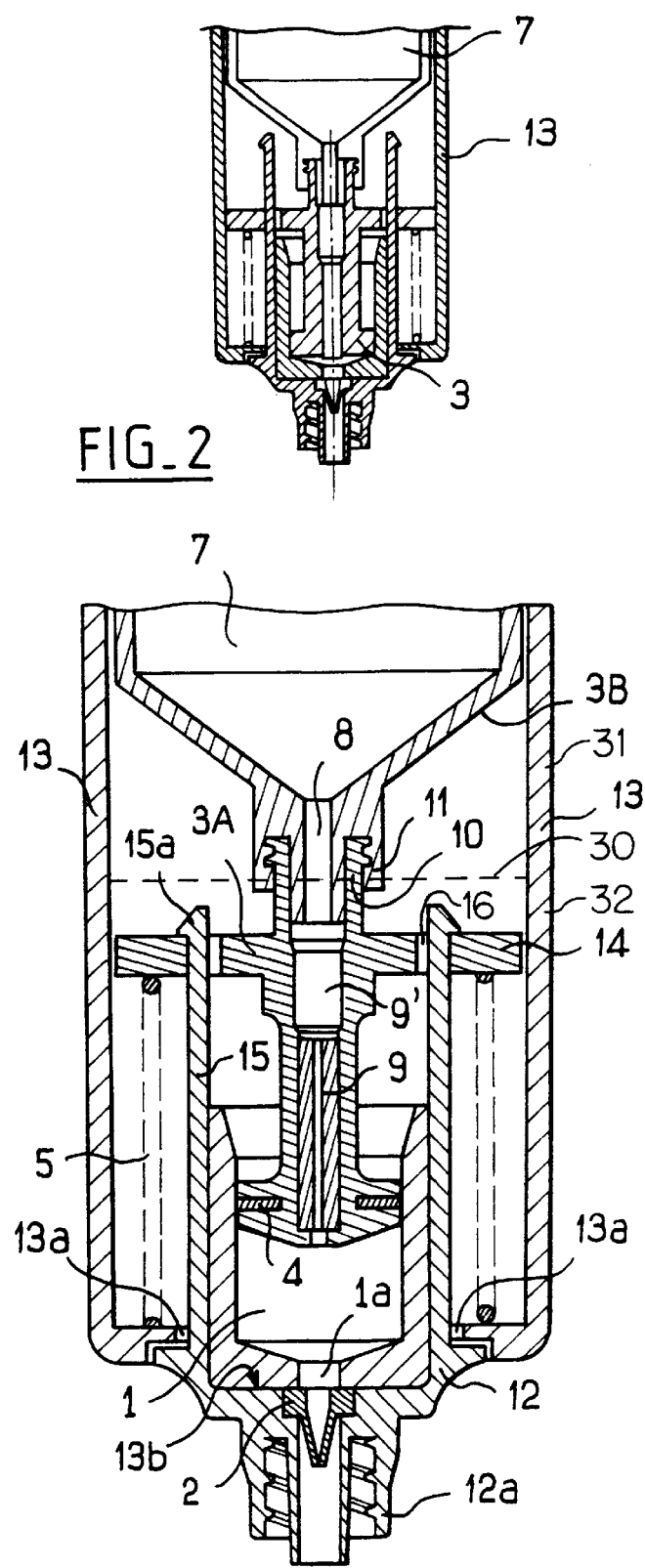
FIG_2
FIG_3

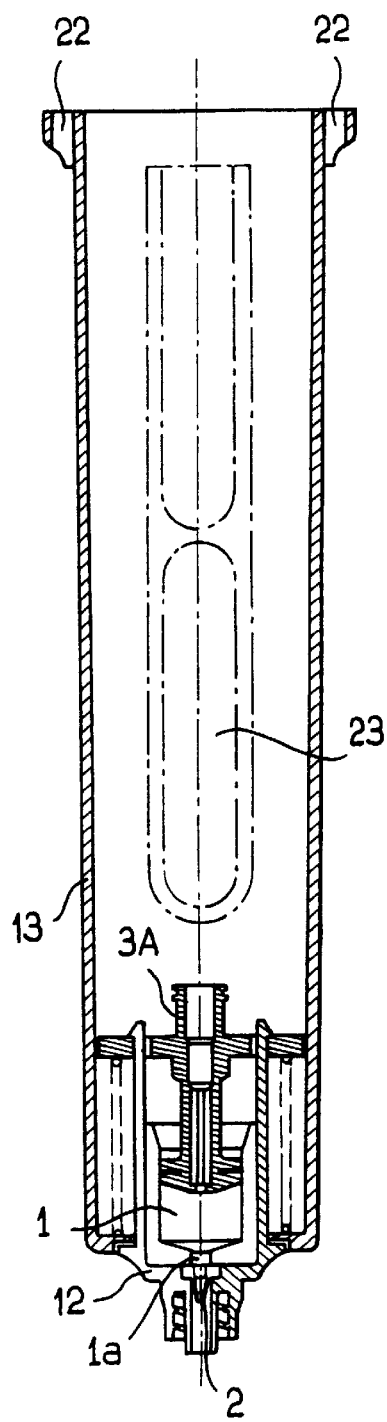
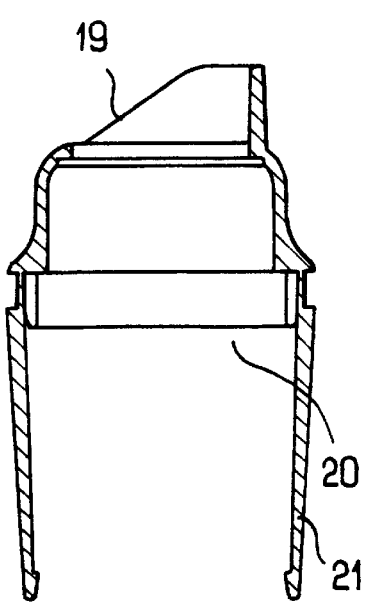
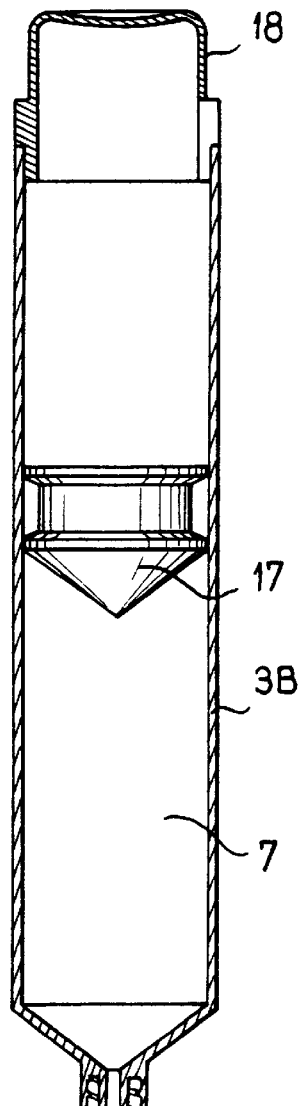
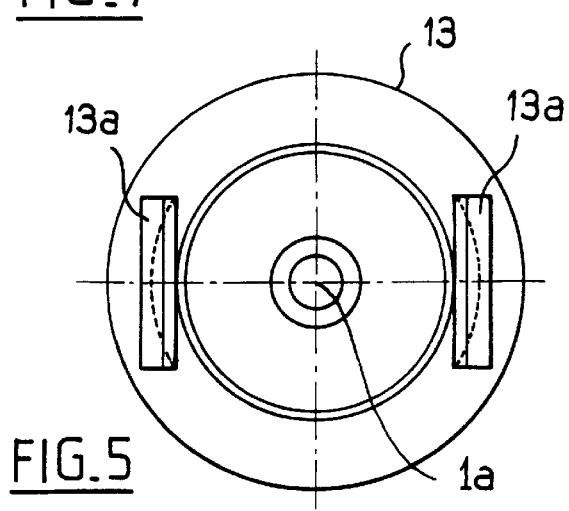
FIG_4  FIG_7  FIG_6  FIG_5

DEVICE FOR INJECTING A LIQUID

The invention relates to a portable and non-implantable device for enabling a patient to self-administer, on demand, successive doses of a liquid while ensuring that the time period between two successive administrations cannot be less than a reference value.

BACKGROUND OF THE INVENTION

Devices are known that comprise:

a chamber provided with an injection outlet;

non-return means co-operating with said outlet;

a rigid piston suitable for being pushed inside the chamber towards said outlet, with lateral sealing around the piston, and suitable for returning in the opposite direction under drive from return means;

means limiting the stroke of the piston in the reverse direction so that the volume of the chamber at the end of the piston return stroke corresponds to the volume of a dose to be administered; and a liquid reservoir having a capacity of several doses and communicating with the chamber via a flow rate limiter corresponding to the reference value.

OBJECTS AND SUMMARY OF THE INVENTION

An object of the invention is to provide a device that is compact, that is easy to handle, and that reduces the risk of accidents.

According to the invention, this is achieved with a device as defined above and in which the liquid reservoir is formed in the piston and communicates with the inside of the chamber via a passage formed through the piston and provided with a flow rate limiter such that the filling time of the chamber by liquid being sucked from the reservoir under the effect of the suction caused in the chamber by return of the piston, corresponds to the reference value.

Preferably, the device comprises a single unit, with all of the components of the device being contained in a tubular case closed by a cover that leaves access to a pusher secured to the piston. The device does not include any external tube that could constitute the cause of an accident, other than the tube connected to its injection outlet.

The case serves to guide the piston, which is mounted to slide inside the case without lateral play.

BRIEF DESCRIPTION OF THE DRAWINGS

One such embodiment is described below by way of non-limiting example, with the description and the figures showing other advantageous features which are included in the embodiment described but which, in variant embodiments, can be used individually or in partial combinations.

In the figures:

FIG. 1 is an axial section through the device, with the piston in its high position;

FIG. 2 is a similar view showing a fragment in which the piston is in its low position;

FIG. 3 is a view on a larger scale of the bottom end of FIG. 1;

FIG. 4 is an axial section through the device from which the disengageable reservoir-forming portion of the piston has been removed, as has the cover of the case of the device;

FIG. 5 is an outside view of the bottom of the case;

FIG. 6 is an axial section of the reservoir-forming portion of the piston that can be dissociated from the remainder of the piston;

FIG. 7 is a section view of the cover of the case of the device; and

MORE DETAILED DESCRIPTION

Figure 8:
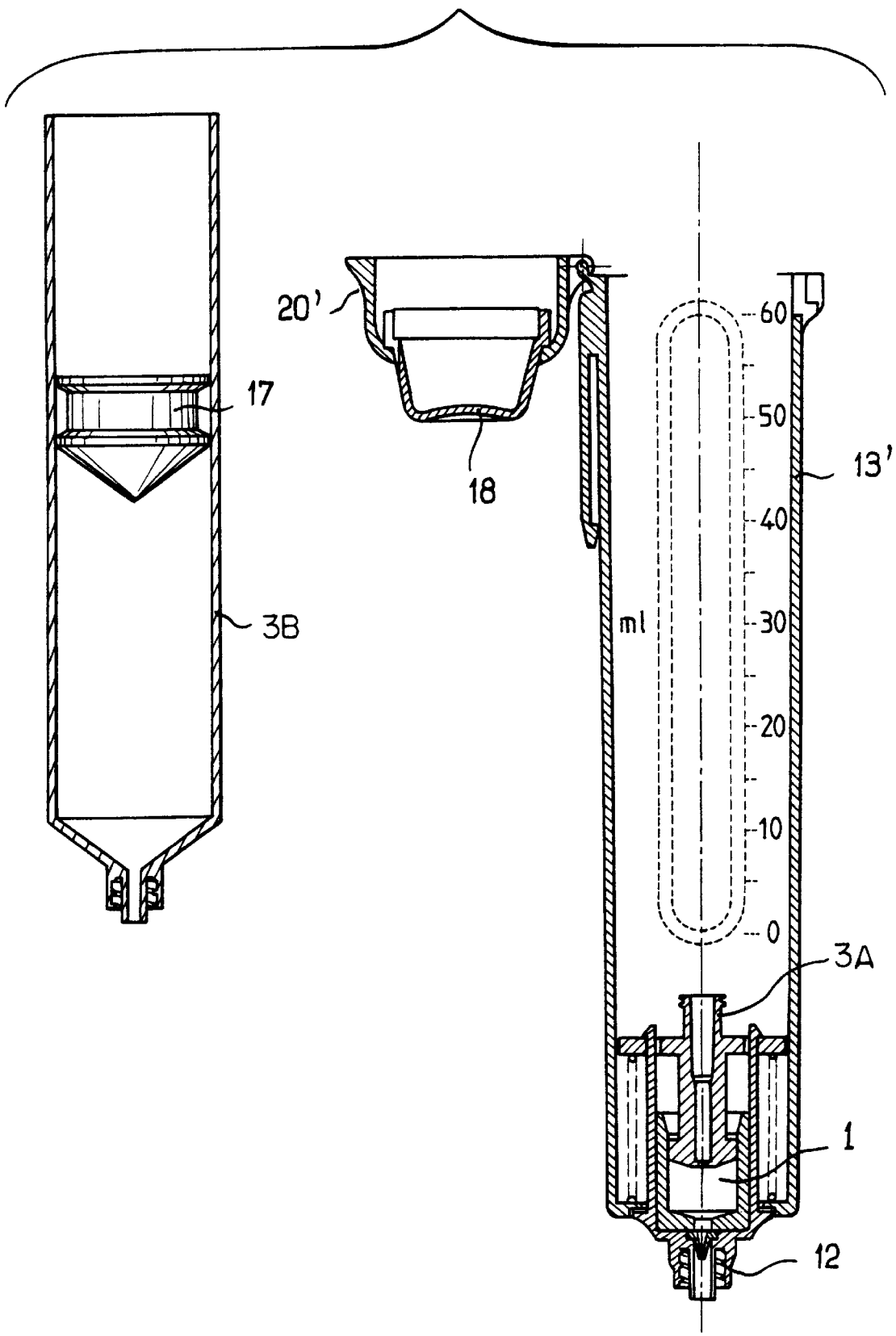
FIG. 8 is an axial section of a variant of the device.

The device shown in the figures is a device in the form of a single unit which comprises a cylindrical case 13 containing:

a chamber 1 provided with an injection outlet 1a;

non-return means 2, e.g. a non-return valve that is known per se, co-operating with the outlet 1a to prevent already-injected liquid being sucked back into the chamber via said outlet during the return stroke of the piston;

a rigid piston 3 suitable for being urged axially inside the chamber towards the outlet 1a, with lateral sealing 4 around the piston, and suitable for returning in the opposite direction under drive from return means, so that at the end of the return stroke (the position shown in FIG. 1), the volume of the chamber corresponds to the volume of a dose to be administered; and a liquid reservoir 7 formed in the piston and communicating with the inside of the chamber 1 via a passage 8 formed in the piston and provided with a capillary tube 9 that is selected as a function of the reference value.

Advantageously, the passage 8 which contains the capillary tube 9 also includes a filter 9' upstream from the capillary.

Advantageously, the piston 3 is constituted by a bottom piston portion 3A which penetrates into the chamber 1 with lateral sealing 4, and a top piston portion 3B which constitutes a cartridge containing said reservoir 7 and which is preferably fixed to the bottom portion by means enabling it to be engaged and disengaged, as is the case in the example shown.

In the example shown, these means comprise a female conical socket 10 formed at the top end of the bottom piston portion 3A and into which there penetrates a male spout 11 formed at the bottom end of the top piston portion 3B, the socket and the spout having co-operating threads to achieve said fixing by screw fastening (FIG. 3).

In this embodiment, the chamber 1 is integrally molded with the case 13, and the bottom of the case has two windows or apertures 13a (FIG. 5) on either side of the chamber and through there pass two arms 15 secured to a piece 12 which is applied against the outside face 13b of the bottom of the case to hold the non-return means 2 against the outlet 1a (FIG. 3) and which has an outlet socket 12a for connection to a tube, in conventional manner.

In this embodiment, the externally-applied piece and the piston include means that co-operate to limit the return stroke of the piston.

For example, the piston 3 includes a cross-member 14 which slides along the arms 15 when the piston moves. At the end of its return stroke, the piston comes into abutment against the ends 15a of the arms, thereby defining the end of its stroke.

The holes 16 through the cross-member 14 are large enough to allow the ends 15a of the arms to pass through them when the piston is installed inside the case, with the arms flexing momentarily.

The return spring 5 is advantageously placed inside the case around the piece 12 and bears against the cross-member.

The cross-member may have any desired shape, e.g. it may be in the form of a disk.

As can be seen in FIG. 1, the reservoir 7 contains a plug 17 which tracks the level of the liquid in the reservoir and prevents any empty space occurring above the liquid in the reservoir, and which also guarantees that the device remains leakproof in any position.

The piston 3 is closed at its top end by a pushbutton 18 which projects from an opening 19 formed in a cover 20 mounted at the top end of the case 13. In the embodiment shown in FIGS. 1 to 7, the cover 20 has arms 21 which are pushed down through passages 22 formed on the side of the case until the top ends of the arms become jammed in the passages, so that in order to remove the cover it is necessary to break the arms. It is therefore not possible to withdraw or replace the cartridge 3B surreptitiously.

In a variant, the cover is mounted in such a manner as to be capable of being opened, as shown in FIG. 8, which is given by way of example and in which the cover 20' is pivotally mounted on the case 13'.

The pushbutton 18 is pierced to admit air into the reservoir above the moving plug so that atmospheric pressure acts on the moving plug.

Advantageously, the case has transparent or pierced portions 23, optionally provided with reference marks, enabling the plug 17 to be observed and consequently indicating the volume of liquid remaining.

Numerous variants of the device are possible. For example, in an advantageous embodiment, the case is constituted by portions that are separable so that the zone where the two portions 3A and 3B of the piston are fixed together is accessible after the case has been disassembled, thereby facilitating action in said zone, particularly when changing the reservoir cartridge 3B. FIG. 3 depicts one embodiment of a separation line 30 along which a conventional separation joint is constructed to create a first separate portion 31 of the case 13 and a second separate portion 32 of the case 13.

In a variant, provision is also made for the chamber to be carried by the piece rather than being secured to the case, in which case the bottom of the case is sufficiently open to enable the chamber to be inserted therethrough.

OPERATION

FIG. 1 shows the device ready for use. Starting from the position shown in FIG. 1, the patient pushes the piston manually until it reaches the end of its stroke at the bottom of the chamber 1 against the outlet 1a, thereby emptying the chamber (FIG. 2).

After the pushbutton 18 has been released, the piston returns almost at once to its initial position (FIG. 1) under drive from the return spring 5.

The chamber 1 is thus subjected to suction since the "duck bill" type non-return valve 2 prevents any fluid entering the chamber via its outlet.

The suction acts via the passage 8 to suck in the liquid contained in the reservoir 7 until the chamber has been filled, and the filling time is determined by the dimensions of the capillary tube placed in this passage.

It is claimed:

1. A portable and non-implantable device for enabling a patient to self-administer, on demand successive doses of a liquid while ensuring that the time period between two successive administrations cannot be less than a reference value determined by the dimensions of a capillary passage, the device comprising:

a chamber provided with an injection outlet;

valve means co-operating with said outlet for preventing already injected liquid from being sucked back into said chamber via said outlet;

a rigid piston suitable for being pushed inside the chamber in the direction of said outlet, with lateral sealing around the piston, said piston including a bottom piston portion that penetrates into the chamber with lateral sealing and a top piston portion that contains a liquid reservoir that is fixed to the bottom portion by means enabling engagement and disengagement, and spring means for returning the piston in the opposite direction;

means limiting the stroke of the piston in the opposite direction so that the volume of the chamber at the end of said stroke corresponds to the volume of a dose to be administered;

the liquid reservoir having a capacity of several doses wherein the liquid reservoir is formed in the top piston portion and communicates with the inside of the chamber via a capillary passage formed through the bottom piston portion and whose dimensions are such that the filling time of the chamber by liquid being sucked from the reservoir under the effect of the suction caused in the chamber by return of the piston corresponds to the reference value; and a tubular case containing the piston and the chamber and closed by a removable cover preventing withdraw of the top piston portion, said cover having an opening leaving access to push the piston.

2. A device according to claim 1, wherein the top piston portion is screwed to the bottom piston portion.

3. A device according to claim 1, wherein the cover has arms which are pushed down through passages formed on the case until top ends of the arms become jammed in the passages whereby removal of the cover necessitates breaking the arms.

4. A device according to claim 1, wherein the chamber is integrally molded with the case.

5. A portable and non-implantable device for enabling a patient to self-administer, on demand, successive doses of a liquid while ensuring that the time period between two successive administrations cannot be less than a reference value determined by the dimensions of a capillary passage, the device comprising:

a chamber provided with an injection outlet;

valve means co-operating with said outlet for preventing already injected liquid from being sucked back into said chamber via said outlet;

a rigid piston suitable for being pushed inside the chamber in the direction of said outlet, with lateral sealing around the piston, said piston including a bottom piston portion that penetrates into the chamber with lateral sealing and a top piston portion that contains a liquid reservoir that is fixed to the bottom portion by means enabling engagement and disengagement, and spring means for returning the piston in the opposite direction;

means limiting the stroke of the piston in the opposite direction so that the volume of the chamber at the end of said stroke corresponds to the volume of a dose to be administered;

the liquid reservoir having a capacity of several doses wherein the liquid reservoir is formed in the top piston portion and communicates with the inside of the chamber via a capillary passage formed through the bottom piston portion and whose dimensions are such that the filling time of the chamber by liquid being sucked from the reservoir under the effect of the suction caused in the chamber by return of the piston corresponds to the reference value; and a case constituted by separable portions to give access to a zone where the top piston portion is fixed to the bottom piston portion, the chamber and the piston being contained in the case.

6. A device according to claim 5, wherein the top piston portion is screwed to the bottom piston portion.

7. A portable and non-implantable device for enabling a patient to self-administer, on demand, successive doses of a liquid while ensuring that the time period between two successive administrations cannot be less than a reference value determined by the dimensions of a capillary passage, the device comprising:

a chamber provided with an injection outlet;

valve means co-operating with said outlet for preventing already injected liquid from being sucked back into said chamber via said outlet;

a rigid piston suitable for being pushed inside the chamber in the direction of said outlet, with lateral sealing around the piston, and spring means for returning the piston in the opposite direction;

means limiting the stroke of the piston in the opposite direction so that the volume of the chamber at the end of said stroke corresponds to the volume of a dose to be administered;

a liquid reservoir having a capacity of several doses wherein the liquid reservoir is formed in the piston and communicates with the inside of the chamber via a capillary passage formed through the piston and whose dimensions are such that the filling time of the chamber by liquid being sucked from the reservoir under the effect of the suction caused in the chamber by return of the piston corresponds to the reference value; and a tubular case containing said chamber and said piston, wherein said means limiting the stroke of the piston includes a piece applied externally against a bottom of the tubular case, said piece having arms that penetrate into the case via apertures formed in the bottom of the case, said arms having ends adapted to contact the piston and thereby limit the stroke of the piston.

8. A device according to claim 7, wherein the piston includes a cross-member that slides along the arms when the piston is pushed, and that comes into abutment against the ends of the arms when the piston is returned in said opposite direction, thereby determining the end of said stroke.

9. A device according to claim 8, wherein said spring means bear against said cross-member.

10. A device according to claim 7, wherein the top piston portion is screwed to the bottom piston portion.

11. A device according to claim 7, wherein the chamber is integrally molded with the case.

12. A portable and non-implantable device for enabling a patient to self-administer, on demand, successive doses of a liquid while ensuring that the time period between two successive administrations cannot be less than a reference value determined by the dimensions of a capillary passage, the device comprising:

a chamber provided with an injection outlet;

valve means co-operating with said outlet for preventing already injected liquid from being sucked back into said chamber via said outlet;

a rigid piston suitable for being pushed inside the chamber in the direction of said outlet, with lateral sealing around the piston, and spring means for returning the piston in the opposite direction;

means limiting the stroke of the piston in the opposite direction so that the volume of the chamber at the end of said stroke corresponds to the volume of a dose to be administered; and a liquid reservoir having a capacity of several doses wherein the liquid reservoir is formed in the piston and communicates with the inside of the chamber via a capillary passage formed through the piston and whose dimensions are such that the filling time of the chamber by liquid being sucked from the reservoir under the effect of the suction caused in the chamber by return of the piston corresponds to the reference value, the portion of the piston that constitutes the reservoir contains a plug that follows the level of the liquid in the reservoir, preventing any empty space existing above the liquid in the reservoir, and guaranteeing that the device is leakproof in any position.

13. A device according to claim 12, wherein the chamber and the piston are contained in a case and wherein the case has portions adapted so that the plug is visible from outside the device so as to indicate the volume of liquid remaining in the reservoir.

14. A device according to claim 12, wherein the piston contains a top piston portion and a bottom piston portion and wherein the top piston portion is screwed to the bottom piston portion.

15. A device according to claim 12, wherein the piston and chamber are contained in a tubular case and wherein the chamber is integrally molded with the case.

16. A portable and non-implantable unit for enabling a patient to self-administer, on demand, successive doses of a liquid while ensuring that the time period between two successive administrations cannot be less than a reference value determined by the dimensions of a capillary passage, the unit comprising:

a tubular case having a bottom end and having a top end;

a chamber in the bottom end of the case provided with an injection outlet to empty the chamber out of the case;

valve means cooperating with said outlet for preventing already injected liquid from being sucked back into said chamber via said outlet;

a piston slidable axially in the case, suitable to be pushed towards said outlet and suitable to return in a reverse direction;

a spring means adapted to force said piston in the reverse direction;

said piston including a bottom piston portion and a changeable top piston portion fixed to one another by fixing means enabling the top portion piston to be engaged and disengaged from the bottom piston portion within the case;

said bottom piston portion penetrating into the chamber with lateral sealing around the bottom piston portion to determine the volume of the chamber;

abutment means to limit the stroke of the bottom piston portion in said reverse direction by abutment of this portion so that the volume of the chamber at the end of said stroke corresponds to the volume of a dose to be administered, said abutment means including arms provided in said case, and wherein said bottom piston portion slides along said arms of said abutment means until coming into abutment against ends of the arms at the end of said stroke; and a liquid reservoir having a capacity of several doses formed within said top piston portion and communicating with the chamber via a capillary passage formed through the bottom piston portion, said capillary passage having dimensions such that the filling time of the chamber by liquid being sucked from the reservoir under the effect of the suction caused in the chamber by said stroke, corresponds to the reference value.

17. A unit as defined in claim 16, wherein the chamber is integrally molded with the case.

18. A unit as defined in claim 16, wherein the top piston portion is screwed to the bottom piston portion by said fixing means.

19. A portable and non-implantable unit for enabling a patient to self-administer, on demand, successive doses of a liquid while ensuring that the time period between two successive administrations cannot be less than a reference value determined by the dimensions of a capillary passage, the unit comprising:

a tubular case having a bottom end and having a top end;

a chamber in the bottom end of the case provided with an injection outlet to empty the chamber out of the case;

valve means cooperating with said outlet for preventing already injected liquid from being sucked back into said chamber via said outlet;

a piston slidable axially in the case, suitable to be pushed towards said outlet and suitable to return in a reverse direction;

a spring means adapted to force said piston in the reverse direction;

said piston including a bottom piston portion and a changeable top piston portion fixed to one another by fixing means enabling the top portion piston to be engaged and disengaged from the bottom piston portion within the case;

said bottom piston portion penetrating into the chamber with lateral sealing around the bottom piston portion to determine the volume of the chamber;

abutment means to limit the stroke of the bottom piston portion in said reverse direction by abutment of this portion so that the volume of the chamber at the end of said stroke corresponds to the volume of a dose to be administered, said abutment means includes a piece applied exteriorly against the bottom end of the case and provided with arms which penetrate into the case through openings formed in said bottom end on either side of the chamber, and wherein said bottom piston portion is provided with a cross-member which slides along said arms, when the piston moves, until coming into abutment against ends of said arms at the end of said stroke; and a liquid reservoir having a capacity of several doses formed within said top piston portion and communicating with the chamber via a capillary passage formed through the bottom piston portion, said capillary passage having dimensions such that the filling time of the chamber by liquid being sucked from the reservoir under the effect of the suction caused in the chamber by said stroke, corresponds to the reference value.

20. A unit as defined in claim 19, wherein the top piston portion is screwed to the bottom piston portion by said fixing means.

21. A portable and non-implantable unit for enabling a patient to self-administer, on demand, successive doses of a liquid while ensuring that the time period between two successive administrations cannot be less than a reference value determined by the dimensions of a capillary passage, the unit comprising:

a tubular case having a bottom end and having a top end;

a chamber in the bottom end of the case provided with an injection outlet to empty the chamber out of the case;

valve means cooperating with said outlet for preventing already injected liquid from being sucked back into said chamber via said outlet;

a piston slidable axially in the case, suitable to be pushed towards said outlet and suitable to return in a reverse direction;

a spring means adapted to force said piston in the reverse direction;

said piston including a bottom piston portion and a changeable top piston portion fixed to one another by fixing means enabling the top portion piston to be engaged and disengaged from the bottom piston portion within the case;

said bottom piston portion penetrating into the chamber with lateral sealing around the bottom piston portion to determine the volume of the chamber;

abutment means to limit the stroke of the bottom piston portion in said reverse direction by abutment of this portion so that the volume of the chamber at the end of said stroke corresponds to the volume of a dose to be administered;

a liquid reservoir having a capacity of several doses formed within said top piston portion and communicating with the chamber via a capillary passage formed through the bottom piston portion, said capillary passage having dimensions such that the filling time of the chamber by liquid being sucked from the reservoir under the effect of the suction caused in the chamber by said stroke, corresponds to the reference value; and a removable cover mounted at the top end of the case to prevent the withdrawal of the top piston portion out of said tubular case, said cover being provided with an opening leaving access to push the piston.

22. A unit as defined in claim 21, wherein the top piston portion is screwed to the bottom piston portion by said fixing means.

23. A unit as defined in claim 21 wherein the cover has arms which are pushed down through passages formed on the side of the case until top ends of the arms become jammed in the passages whereby removal of the cover necessitates breaking the arms.

* * * * *